US009028751B2

(12) United States Patent
Pagé et al.

(10) Patent No.: US 9,028,751 B2
(45) Date of Patent: May 12, 2015

(54) SYSTEM AND METHOD FOR DYNAMICALLY CONTROLLING ODOR EMISSION

(75) Inventors: Thierry Pagé, Montréal (CA); Philippe Barnéoud, Montréal (CA); Philippe G. Micone, Montréal (CA); Delphine F. Courmier, Montréal (CA)

(73) Assignee: Odotech Inc., Montréal (CA)

( * ) Notice: Subject to any disclaimer, the term of this patent is extended or adjusted under 35 U.S.C. 154(b) by 0 days.

(21) Appl. No.: 12/500,011

(22) Filed: Jul. 9, 2009

(65) Prior Publication Data

US 2011/0009986 A1    Jan. 13, 2011

(51) Int. Cl.
*G01W 1/02* (2006.01)
*G06F 19/00* (2011.01)
*G01N 27/00* (2006.01)
*G01N 33/00* (2006.01)

(52) U.S. Cl.
CPC ............. *G01N 33/0031* (2013.01); *G01W 1/02* (2013.01)

(58) Field of Classification Search
CPC ............................ G01N 33/0031; G01W 1/02
USPC ................................ 422/62; 73/23.34; 700/90
See application file for complete search history.

(56) References Cited

U.S. PATENT DOCUMENTS 3,744,043 A * 7/1973 Walden et al. ............ 340/870.07
3,924,605 A * 12/1975 Weinman et al. ............ 126/307 A
4,817,039 A * 3/1989 Frost ................................. 702/3
5,137,687 A   8/1992 Dunson, Jr.
5,767,385 A   6/1998 Bundy et al.
5,801,297 A   9/1998 Mifsud et al.
6,068,686 A * 5/2000 Sorensen et al. ................ 96/135
6,277,239 B1   8/2001 Kemper et al.
6,277,329 B1   8/2001 Evans
6,290,838 B1   9/2001 Mifsud et al.

(Continued)

FOREIGN PATENT DOCUMENTS

CA    2675173    7/2008
GB    2191914    12/1987
WO    9912028    3/1999

OTHER PUBLICATIONS

"Microcontroller—Wikipedia, the free encyclopedia", http://en.wikipedia.org/wiki/Microcontroller, Nov. 24, 2011.

(Continued)

*Primary Examiner* — Paul Hyun
(74) *Attorney, Agent, or Firm* — Bereskin & Parr LLP/S.E.N.C.R.L., s.r.l.

(57) ABSTRACT

The present invention relates to a system and method for dynamically controlling odor emission. The system comprises an odor measurement tool, a weather condition measurement tool, a processing module and a controller. The odor measurement tool is adapted to measure an odor level. The weather condition measurement tool is adapted to measure at least one weather condition. The processing module is adapted to calculate an odor emission threshold based on the measured odor level, the at least one weather condition, an atmospheric dispersion model and a predetermined remote odor level threshold. The controller is adapted to control the odor emission below the odor emission threshold.

32 Claims, 5 Drawing Sheets

(56) References Cited

U.S. PATENT DOCUMENTS

| | | | |
|---|---|---|---|
| 6,411,905 B1* | 6/2002 | Guoliang et al. | 702/23 |
| 6,495,341 B1 | 12/2002 | Zenhausern | |
| 6,496,742 B1 | 12/2002 | Labreche et al. | |
| 6,496,813 B1 | 12/2002 | Labreche et al. | |
| 6,590,496 B2* | 7/2003 | Peterson et al. | 340/522 |
| 6,975,944 B1 | 12/2005 | Zenhausern | |
| 6,981,947 B2 | 1/2006 | Melker | |
| 7,097,973 B1 | 8/2006 | Zenhausern | |
| 7,114,388 B1* | 10/2006 | French et al. | 73/170.16 |
| 7,522,963 B2 | 4/2009 | Boyden et al. | |
| 2002/0094531 A1 | 7/2002 | Zenhausern | |
| 2004/0166043 A1* | 8/2004 | Vandine et al. | 423/245.1 |
| 2005/0064585 A1 | 3/2005 | Wolf et al. | |
| 2005/0208673 A1 | 9/2005 | Labreche et al. | |
| 2006/0065117 A1 | 3/2006 | Jain | |
| 2006/0151395 A1 | 7/2006 | Gavaskar et al. | |

OTHER PUBLICATIONS

Nakamoto, "Odor Handling and Delivery Systems", Mar. 2003, Chapter 3, pp. 55-78.

Schiffman et al., "Analysis of Medication Off-odors Using an Electronic Nose", Chem. Senses 22: pp. 119-128, (1987).

Ampuero et al., "The electronic nose applied to dairy products: a review", Sensors and Actuators, B94, pp. 1-12, (2003).

Tanaka et al., "Clinical Assessment of Oral Malodor by the Electronic Nose System", J. of Dent. Res 83(4), pp. 317-321, (2004).

* cited by examiner

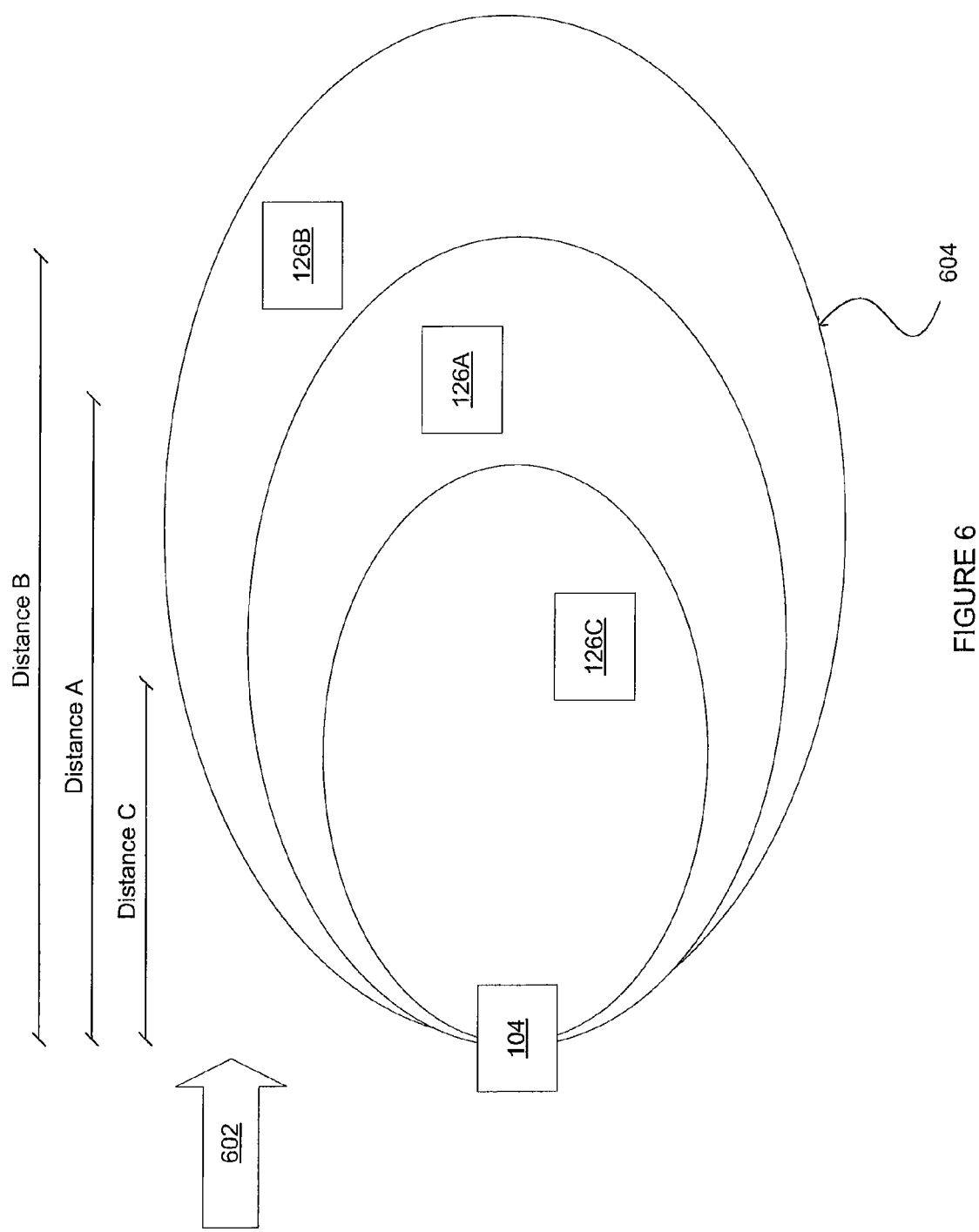

SYSTEM AND METHOD FOR DYNAMICALLY CONTROLLING ODOR EMISSION

FIELD OF THE INVENTION

The present relates to a system and method for dynamically controlling odor emission.

BACKGROUND OF THE INVENTION

Nowadays, as global population density increases, residential properties encroach closer and closer to land that is in close proximity of agricultural and industrial enterprises. Some of those enterprises are well known for producing unpleasant odor emissions. In some instances, the unpleasant odor emissions produced by those enterprises corresponds to pollutants released in the surrounding environment. Therefore, various groups such as local residents, environmental groups and governments have been pressuring enterprises to lower their emissions of pollutants for health reasons, and of odor emission for comfort reasons.

So far, various systems that lower odor emissions have been developed. However, even with governmental grants, enterprises find them costly to purchase and to maintain. Most systems use chemicals or energy that reduces odor level in an emission. Often, for better results, the systems can be used in combination with other systems, however all systems require maintenance and replenishing, thus the more it is used the costlier it is for the enterprise.

SUMMARY OF THE INVENTION

In accordance with an aspect of the present invention, there is provided a system for dynamically controlling odor emission at an emission site. The system comprises an odor measurement tool, a weather condition measurement tool, a processing module and a controller. The odor measurement tool is adapted to measure an odor level. The weather condition measurement tool is adapted to measure at least one weather condition. The processing module is adapted to determine an odor emission threshold based on the measured odor level, the at least one weather parameter, an atmospheric dispersion model and a predetermined remote odor threshold.

In accordance with another aspect of the present invention, there is provided a method for dynamically controlling odor emission. The method comprises measuring an odor level, measuring at least one weather parameter, calculating an odor emission threshold using the measured odor level, measured at least one weather condition and an atmospheric dispersion model, and controlling the odor emission below the odor emission threshold.

BRIEF DESCRIPTION OF THE DRAWINGS

For a better understanding of aspects of the system and method described herein, and to show more clearly how they may be carried into effect, reference will be made by way of example, to the accompanying drawings in which:

FIG. 6 is a graphical representation of odor dispersion over a geographical area including three remote sites.

DETAILED DESCRIPTION OF THE INVENTION

The present relates to a system and method for dynamically controlling odor emission, such as for example at an odor emission chimney, at a ventilation exhaust, or an air freshener to cover an undesired odor. More particularly, the present relates to dynamically controlling odor according to various parameters indicative of how the odor is dispersed in a surrounding environment.

For clarity purposes, the following terminology is used throughout the present specification and claims:

odor: the sensorial perception of an odorant substance;

odor emission: release of odorant substance;

odor level: used broadly to refer to quality and/or quantity of an odor, examples of odor levels include: odor concentration, odor intensity, odor degree, odor dilution to threshold, odor index, odor hedonic level, odor nuisance factor, or any other means of representation of a level of odor;

odor emission threshold: an odor level threshold for odor emission;

odor concentration: one type of odor level, used to quantify odors. Examples of standards include European standard EN 13725:2003 "Air quality—Determination of odor concentration by dynamic olfactometry", ASTM International Designation E 1432-04 "Standard Practice for Defining and Calculating Individual and Group Sensory Thresholds from Forced-Choice Data Sets of Intermediate Size" and VDI 3882 Handbuch Reinhaltung der Luft, Band 1 "Olfactometry—Determination of Hedonic Odour Tone";

odor flow rate: calculated value using the following equation:

$$\text{odor concentration} \times \text{volume flow rate} = \text{odor flow rate};$$

and

Figure 1:
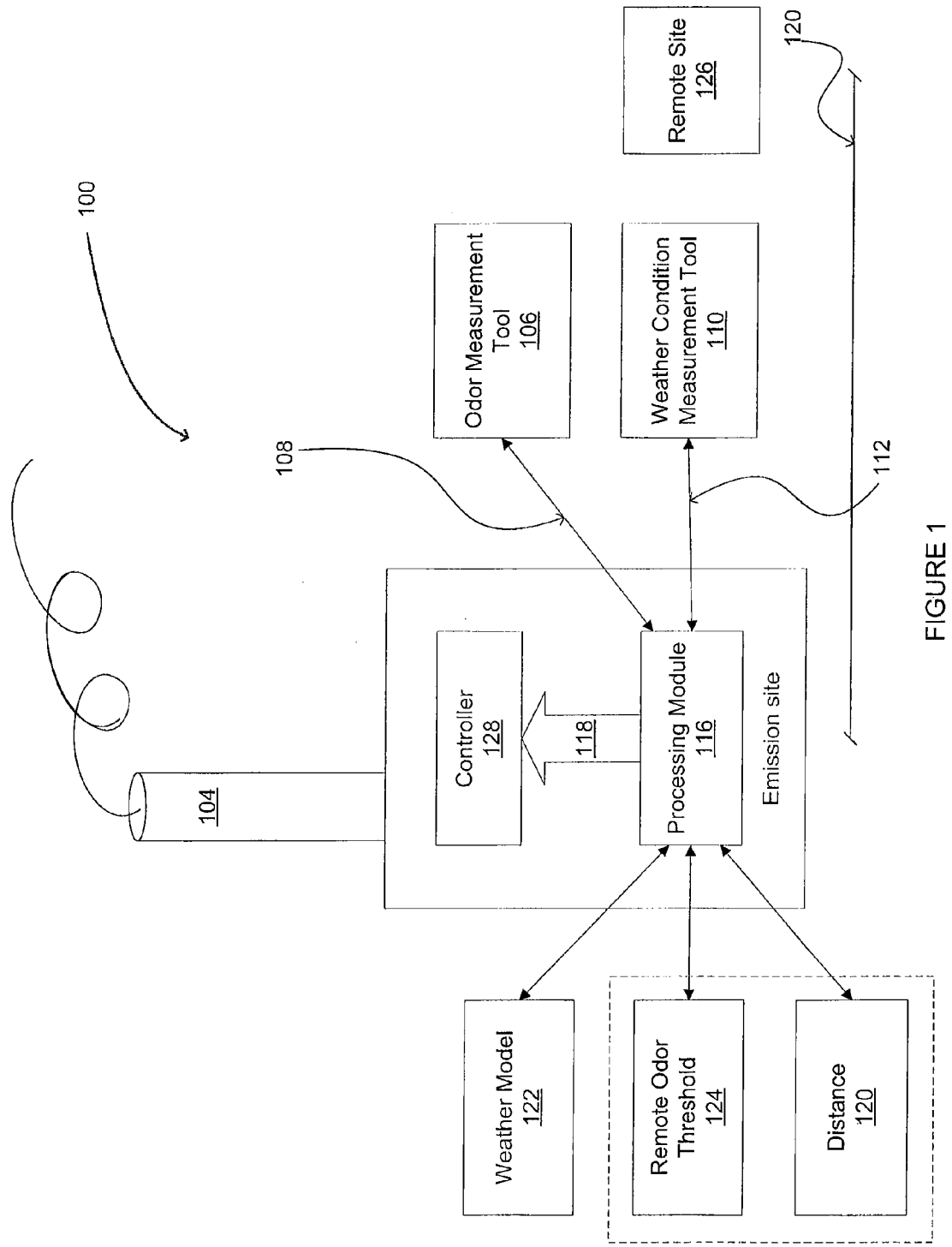
FIG. 1 is a block diagram of a system for dynamically controlling odor emission.

Presented in FIG. 1a is a system 100 for dynamically controlling odor emission 102 at an emission site 104. The emission site 104 may be any type of enterprise or establishment that releases an odor. For dynamically controlling the odor emission, the system 100 comprises an odor measurement tool 106, a weather condition measurement tool 110, a processing module 116 and a controller 128.

The odor measurement tool 106 is adapted to measure an odor level 108. The odor measurement tool 106 could also be adapted to calculate an odor flow rate. The odor measurement tool 106 may be located directly at the emission site 104 or remotely located. More particularly, the odor measurement tool 106 can be located in the emission site 104, in an outlet releasing the odor in the environment, adjacent to the outlet releasing the odor, remotely from the emission site, or at a remote site 126. The odor measurement tool 106 may further consist of a network of measurement tools strategically located in the periphery of the emission site. The odor measurement tool 106 may be electronically or wirelessly connected to the processing module 116. A standardized protocol or a custom defined protocol may be used for achieving the communication there between. The processing module 116 is informed of the location of the odor measurement tool 106, and adapts treatment of received odor level 108 accordingly. Depending on the environment, topography, nature of the odor emission, proximity of remote sites 126 and atmospheric conditions, it could be advantageous to use one or several odor measurement tools 106. However, for clarity purposes, the present specification will only refer to one odor measurement tool 106.

The odor measurement tool 106 may be any type of odor sensing device. Depending on the odor to be measured, various odor measurement tools could also be used. The odor measurement tool 106 may thus be adapted to measure one odor level 108 in particular, or a plurality of odor levels. The odor measurement tool 106 may thus report to the processing module 116 a single odor level or a plurality of odor levels. More particularly, in one aspect, the measurement tool 106 is an electronic nose. Electronic noses are electronic sensing devices adapted to replace human senses by means of sensor arrays and mathematical algorithms for detecting, recognizing and quantifying odors. Manufacturers of electronic noses include Odotech Inc., Dr. Feodisch, Sacmi, MnCo, Air Sence, UltraSens, Smiths Detection, QualSec, Alpha MOS, Bloodhound Sensors Limited, Osmetech plc, Zellweger Luwa Ltd, and Electronic Sensor Technology.

The weather condition measurement tool 110 is adapted to measure at least one weather parameter 112. The weather condition measurement tool 110 may be any type of weather condition metering tool such as an anemometer, a wind vane, a hygrometer, a barometer, a thermometer, etc, or a combination thereof. The weather condition measurement tool 110 may be located at the emission site 104, at a remote site 126, or at any other location. The weather condition measurement tool 110 may further consist of software adapted to download from an official weather center one or several weather parameters currently in condition or on an hourly, a daily basis, or forecasted weather parameters. Alternately, the at least one weather parameter 112 could be calculated by means of an atmospheric model. Using a measured weather condition in another location, such as an official weather base, some atmospheric model can calculate a corresponding weather parameter 112 at the emission site or surrounding environment. Thus although the present description refers to measuring the weather parameter 112, it is not limited to measuring the weather parameter 112 and further includes calculating the weather parameter 112.

Depending on the location of the weather condition measurement tool 110, the system 100 interprets the at least one weather parameter 112 accordingly. The weather condition measurement tool 110 may be in direct or ultimate electronic communication with the processing module 116, or may communicate with the processing module 116 wirelessly through a system of antennas and transceivers. A standardized protocol or a custom defined protocol may be used for achieving the communication there between.

The processing module 116 is adapted to calculate an odor emission threshold 118 to be applied at the emission site 104 based on various factors: measured odor level 108, the at least one weather parameter 112, an atmospheric dispersion model 122 and an acceptable odor level at the remote site 126.

The processing module 116 is adapted to receive directly or ultimately the measured odor level 108 from the odor measurement tool 106 and the at least one weather parameter 112 from the weather condition measurement tool 110. The processing module 116 may be further adapted to receive or retrieve from a database at least one distance input indicative of a distance 120 between the odor emission site 104 and at least one remote site 126. In one aspect, the distance corresponds to a perimeter defined around the emission site. In another aspect, the distance corresponds to a geographical area defined with respect to the emission site. The geographical area or perimeter may correspond to an area in which an acceptable odor threshold must be respected. The database may further store topographical information, which affects dispersion of odor. In another aspect, an acceptable remote odor threshold 124 is also stored in the database for each remote site. In the event that multiple remote sites 126 are to be considered, the distance between the emission site 104 and each of the remote sites is collected and stored in a database, together with an acceptable remote odor threshold 124 for each remote site. The database could further include information as the geographical location of the remote site with respect to the emission site, Reference is now made to FIG. 6, which is a graphical representation of odor dispersion over a geographical area including three remote sites. Wind 602 pushes odor emission away from the emission site 104 forming zones 604 of odor levels. Depending on the wind direction and wind speed, the shape and size of the zones vary, resulting in different odor levels at the three remote sites 126A-126C. Distance between the emission site 104 and the remote sites 126A-126C and topography also affect the odor level detected at each remote site 126A-126C.

It is also possible to store multiple remote odor thresholds 124 for each remote site. These multiple remote odor thresholds could be based on a period of year or a time of day. In one example, the remote odor threshold 124 may be lower in a summer period than in a winter period. During the summer period, it may be more important for local residents to breath air carrying less odor as they may spend a greater part of their day outside. In another example, the threshold 124 may be lower in a peak tourism period. During such period, it may be important for a tourism area to have air carrying less odor for tourists to feel at ease and for encouraging them to come back. Various other aspects could also be considered, such as varying the level of odor levels based on temperature, humidity, etc.

The remote site 126 may consist for example of a natural reserve, a tourist attraction, one or several residential properties, a building, a school, a hospital, or any other type of location for which an acceptable odor threshold has been established or must be respected. It is possible with the present system to have different acceptable odor threshold for remote sites surrounding the emission site.

To determine the impact of weather on odor emission by the emission site, the processing module 116 applies the at least one measured weather parameter 112 to the atmospheric dispersion model 122. The atmospheric dispersion model 122 is a mathematical representation of impacts of weather on gas/pollutant/odor dispersion in the atmosphere, Various types of atmospheric dispersion models exist and are known in the art, such as: AERMOD, ARIA IMPACT, ARIA RISK, ARIA LOCAL, ARIA INDUSTRY, ARIA REGIONAL, ARCON96, AUSTAL2000, BLP, CAL3QHC/ CAL3QHCR, CALINE3, CDM2, COMPLEX1, CTDMPLUS, CTSCREEN, DIMULA, EDMS, ISCST3, ISC-.PRIME, KAPPA-G, LONGZ, OCD, OMEGA/ ADM, PAL-DS, PPSP, PTPLU, RAM, RTDM3.2, SCREEN3, SDM, SHORTZ, TUPOS, VALLEY, ADMS-3, ADMS-Roads, ADMS-Screen, ADMS-Urban, AEROPOL, AVACTA II, DISPERSION, IFDM, MIMO, OML, OND 86, Simple Line Source, SYMOS97, WYND-VALLEY, CALPUFF, HYSPLIT, MESOPUFF-II, SCIPUFF, CALPUFF View, HOTMAC/ RAPTAD, LADM. Any type of atmospheric dispersion model, which is adapted to represent the impact of weather on dispersion of gas, pollutant or odor dispersion, may be used. Depending on the accuracy required, a simpler or more complex atmospheric dispersion model may be used. To obtain a more accurate evaluation of dispersion, a plurality of weather conditions 112 measurement is used for example: wind velocity, wind direction, wind fluctuation, solar radiation, humidity level, barometric pressure, ambient temperature and atmospheric stability classification.

Based on the measured odor level 108, on the at least one weather parameter 112, on the atmospheric dispersion model 112 and the remote odor threshold 124, the processing module 116 calculates a maximum odor emission threshold 118 to be applied at the emission site 104. In the case that multiple remote sites have to be considered, wind direction and geographical location of the remote sites are also considered in the calculation. The processing module 116 provides the odor emission threshold 118 to the controller 128. The controller 128 is adapted to control the odor emission 102 below or equal to the odor emission threshold 118. For doing so, the controller 128 may modify one or several parameters of the emission site, such as for example: ventilation flow, speed of out-stream gases, effluent temperature, amount of chemical reactants used, fuel admission, recycling rate of the chemicals, redox potential, pH, adjustment of air freshener, etc. Thus, the odor emission 102 is dynamically adjusted to remain within acceptable level at each remote site, while optimizing the operation of the emission site, In odor emitting industries, deodorizing processes using chemicals, filters, ventilation systems or odor controlling mechanisms are used to control odor emission. By dynamically adjusting the odor emission threshold 124 as a function of the weather as previously described, it is possible to more efficiently use the deodorizing processes and odor controlling mechanisms, and to reduce chemicals, filters, odor controlling mechanisms, energy consumption or a combination thereof.

The present applies to any deodorization process. Examples of deodorization processes known in the art, include: burners, biofilters, biotrickling filters, bioscrubbers, chemical scrubbers and chemical neutralizers, ion generator, etc.

Thermal oxidizers, also known as burners, are flares, which openly combust gas with ambient or forced air, or incinerators using an enclosed combustion process.

Biofilters use microorganisms to remove air pollution. The air flows through a packed bed and the pollutant transfers into a thin bio-film on the surface of the packing material. Microorganisms, including bacteria and fungi are immobilized in the bio-film and degrade the pollutant. Industries employing the technology include food and animal products, off-gas from wastewater treatment facilities, pharmaceuticals, wood products manufacturing, paint and coatings application and manufacturing and resin manufacturing and application. There is no secondary pollution (unlike the case of incineration where additional $CO_2$ and NOx are produced from burning fuels) and degradation products form additional biomass, carbon dioxide and water. Biotrickling filters and bioscrubbers absorb gas pollutants in a free liquid phase prior to their biodegradation by microorganisms.

Scrubber systems are a diverse group of air pollution control systems that can be used to remove particulates and/or gases from industrial exhaust streams. Traditionally, the term 'scrubber' has referred to pollution control devices that use liquid to 'scrub' unwanted pollutants from a gas stream. In the context of the present system, the term 'scrubber' is used to describe systems that inject a dry reagent, liquid or slurry into a dirty exhaust stream to 'scrub out' gases. Scrubbers are one of the primary devices that control gaseous emissions. In a wet scrubber, the polluted gas stream is brought into contact with the scrubbing liquid, by spraying it with the liquid, by forcing it through a pool of liquid, or by some other contact method, so as to remove the pollutants. Wet scrubbers remove pollutant gases by dissolving or absorbing them into the liquid. A wet scrubber's ability to collect small particles is often directly proportional to the power input into the scrubber. Some disadvantages of wet scrubbers include corrosion, chemical consumption, high power requirements, and the need for treatment or reuse of spent liquid. Indeed, high collection efficiencies for particulate matter are attainable only at high pressure drops, resulting in high operating costs and dewatering and drying of scrubber sludge make recovery of any dust for reuse very expensive and difficult. Wet scrubbers can achieve high removal efficiencies for either particles or gases and, in some instances they can achieve high removal efficiency for both pollutants in the same system. However, in many cases, the best operating conditions for particles collection are the poorest for gas removal. A continuous monitoring of the stream would allow treating the pollution accordingly and achieve better efficiency.

For big open-air sources, such as compost windrows, waste water basins, lagoon, piles or landfill cells, chemical neutralizers are sometimes used. There is a broad range of chemicals used to neutralize the compounds causing the odor, or alternatively masking the odor by releasing other, overshadowing odors that are perceived as pleasant. This process could be adapted when the concentration of odors varies. Hence, a high level of chemicals, such as surfactants, essential oils, perfumes, calcium carbonate, calcium oxide, magnesium hydroxide, and sodium bicarbonate, is currently used, while a dynamic control of odor emission could noticeably reduce use of chemicals.

Other deodorizing processes that could be controlled by the present system include absorbers, condensers, membranes, catalytic reduction, ionizers, ozometers, photocatalytic, and catalytic oxidizers.

According to an aspect, the present system is applied to a scrubber. By dynamically controlling odor emission, it is possible to more efficiently use the scrubber and save energy for the production of ozone $O_3$, while decreasing the amount of chemicals used such as for example sodium hypochlorite NaClO that produces poisonous byproducts. In addition, the present system provides a way to efficiently manage odor nuisances on the neighbors.

Operation of a scrubber typically requires high energy and a large amount of chemicals. More particularly, in the case of ozone, special handling is required as ozone cannot be stored and transported like other industrial gases because it quickly decays into diatomic oxygen and therefore it must be produced on site. At production capacities higher than 20 kg per hour, a gas/water tube heat-exchanger may be utilized as ground electrode and assembled with tubular high-voltage electrodes on the gas-side. The regime of typical gas pressures is around 2 bars absolute in oxygen and 3 bars absolute in air. Several megawatts of electrical power may be installed in large facilities, applied as one phase AC current at 50 to 8000 Hz and peak voltages between 3,000 and 20,000 volts. Therefore, reduction of ozone needs constitutes an important saving to an operator of the scrubber.

In addition to deodorization processes previously discussed, the present system and method can further be applied to a particular category of odor controlling devices: air fresheners. Air fresheners are products that mitigate unpleasant odors. Air fresheners typically work in one of the following five ways:
1. Adsorption: Adsorbents like activated charcoal or silica gel used to absorb offending, chemical odors.
2. Chemical neutralization: Substances such as rubber or TEG used for some odors.

3. Disinfection. Odors caused by bacterial activity can be eliminated by disinfectants like ozone, TEG, or bleaching agents containing hydrogen peroxide, chlorine or hypochlorites.
4. Masking: Many "fresheners" obscure odors with a fragrance.
5. Anesthetization: Some air fresheners use anesthetics to dull the sense of smell.

According to another aspect, the controller 128 is adapted to control a fan of a ventilation exhaust, based on the odor emission threshold 118. When the measured odor level 108 is below the calculated odor emission threshold 118, the controller 128 increases the velocity of the fan to release a higher level of odor. However when the measured odor level 108 is above the odor emission threshold 118, the controller reduces the velocity of the fan to release a lower level of odor. Energy consumption for running the fan is thus used efficiently and only as it is necessary.

According to another aspect, the controller 128 is adapted to control a chemical filter, by varying an amount of chemicals used. When the measured odor level 108 is below the calculated odor emission threshold 118, the controller 128 reduces the amount of chemicals in the chemical filter to release a higher quantity of odor. However when the measured odor level 108 is above the odor emission threshold 118, the controller increases the amount of chemicals in the chemical filter to release less odor. By doing so, the general practice of overusing chemicals is prevented.

According to yet another aspect, the controller 128 is adapted to control a feed mixture for livestock, by varying an amount of odor inhibiting feed additive therein. When the measured odor level 108 is below the odor emission threshold 118, the controller 128 reduces the amount of feed additive in the feed mixture. When the measured odor level 108 is above the odor emission threshold 118, the controller increases the amount of feed additive in the feed mixture. The present system thus prevents overuse of the feed additive and consequently reduces production costs.

Those skilled in the art will understand that there may be other ways for the controller 128 to control odor emission 102 such as for example a ventilation rate of a bio-filter or a compost windrow. Moreover, depending on the area of application, it is possible for the controller 128 to control, in combination, more than one odor emission 102. For example, in the context of a swine producing enterprise, based on the odor emission threshold 118, the controller 128 may control both a fan and a feed mixture.

Figure 2:
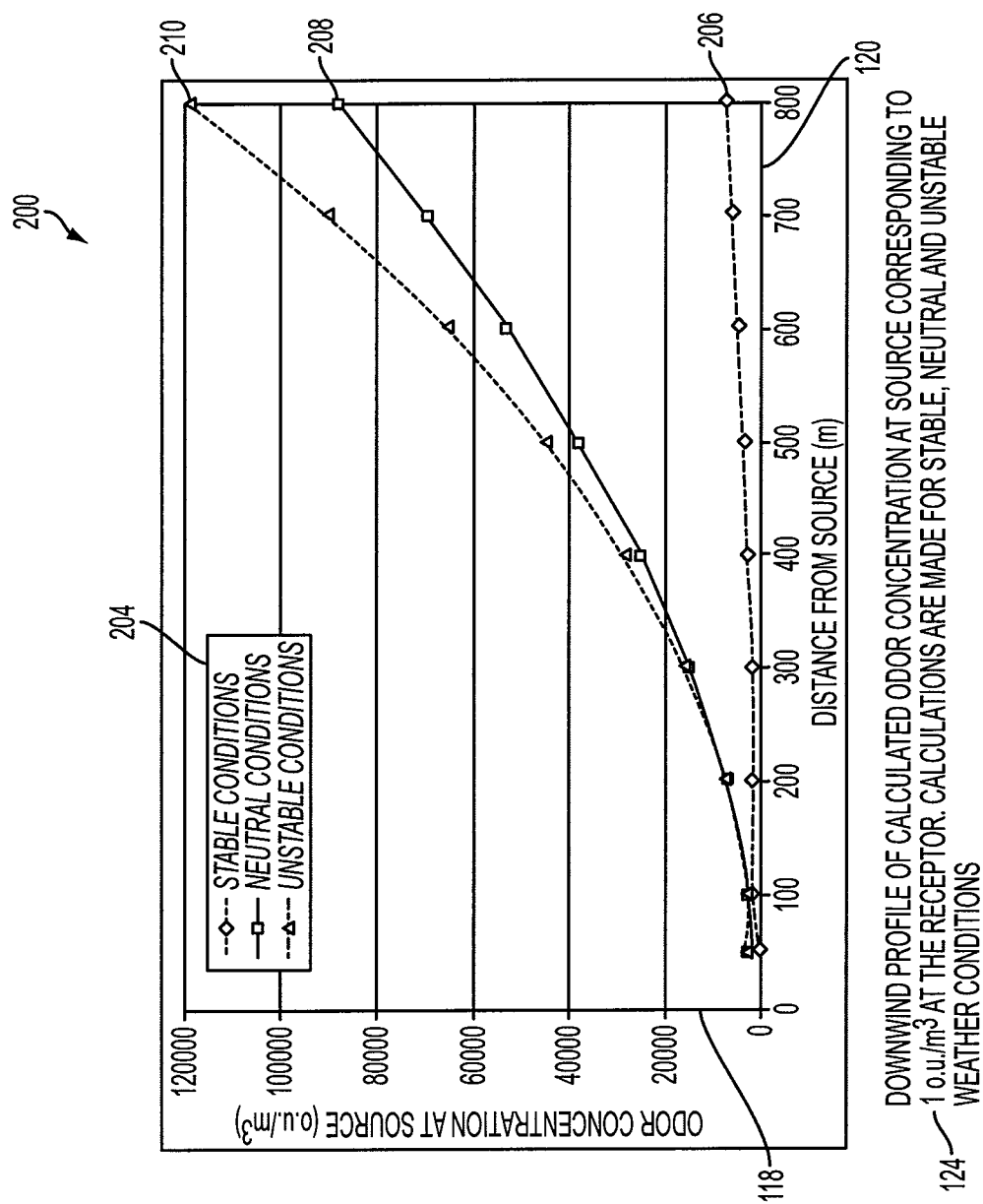
FIG. 2 is a graphical representation of a simulation of the effect of weather conditions on odor dispersion in the environment.

Presented in FIG. 2 is a graphical representation 200 of a simulation of odor dispersion as a function of distance for different weather conditions. Based on this simulation, it is demonstrated that, odor dispersion is affected by weather conditions. More particularly, FIG. 2 represents a downwind profile of calculated odor level at source corresponding to 1 odor unit per cubic meter at a remote site. The calculations were performed for three different weather conditions types 204: stable conditions, neutral conditions and unstable conditions.

Figure 3:
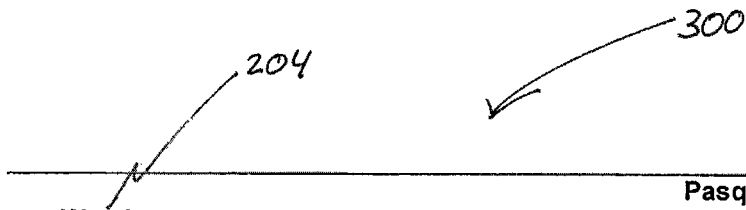
FIG. 3 is a table representing various weather condition types, used for the simulation of FIG. 2.

FIG. 3 is a table 300 defining the parametric values for each of the three weather conditions 204 used in the simulation of FIG. 2. The weather condition types 204 are based on an environment parameter (rural or urban), a wind velocity, a Pasquill-Gifford stability class and an ambient temperature.

Figure 4:
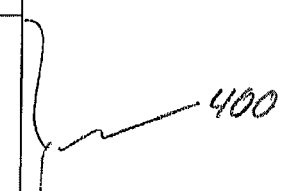
FIG. 4 is a table representing other parameters used for the simulation of FIG. 2.

FIG. 4 provides a table defining other parameters that were used to obtain the simulation results of FIG. 2. These parameters include an emission source type 402, an emission site height 404, an emission site area such as an emission site diameter 406, gas speed 408, gas temperature 410 and a volume flow 412.

In the context of a chimney, the emission site height 404 is the elevation of the chimney from either ground level or sea level, depending on the system 100. Admittedly, the emission site diameter 406 is the opening diameter of the chimney. The gas speed 408 is the velocity with which the odor 102 is released from the chimney. The gas temperature 410 is the temperature of the gas released from the chimney. And finally, the volume flow 412 is the volume of odor released from the chimney during a given period of time.

By taking the emission site parameters and remote site parameters into consideration, in combination with the weather parameter 112, the odor level 108, and the atmospheric dispersion model 122, the processing module 116 is able to dynamically determine the odor emission threshold 118 based on current weather conditions, and with a higher level of accuracy, This allows greater savings in energy, maintenance and replenishing costs.

Figure 5:
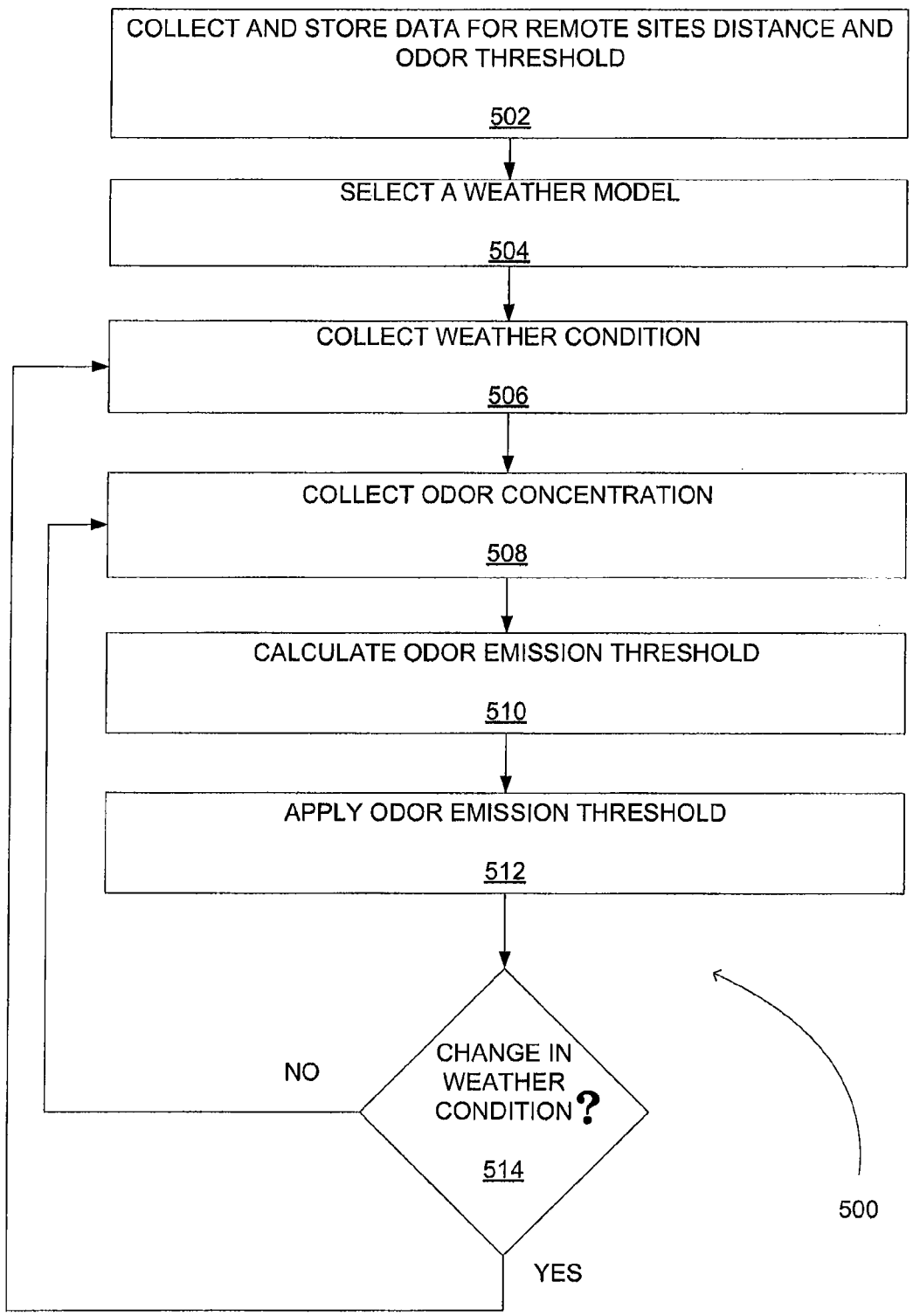
FIG. 5 is a block diagram of a method for dynamically controlling odor emission.

Presented in FIG. 5 is a method 500 for dynamically controlling odor emission. The method 500 comprises collecting and storing data 502 for remote sites such as for example distance, topography and maximum remote odor level threshold. The collection and storage of data 502 is typically performed when the system is installed, or when new remote sites need be added, or a new remote odor level threshold 124 has to be recorded. Then, an atmospheric dispersion model is selected 504. In the instance where the system provides only one atmospheric dispersion model, the step of selecting the atmospheric dispersion model is skipped. Then, the at least one weather parameter 112 is collected 506, and the odor level 108 is collected 508. The method continues with calculating odor emission threshold 118, as previously described. Then, the method applies 512 the odor emission threshold 118 to the controller 128 of the emission site. Verification is then made as to whether there is a change in weather condition 514. In the event that there is no change in the weather condition, the method reverts to the collection 508 of odor level 108, calculation 510 of odor emission threshold 118 and application 514 of the odor emission threshold 118. In the event that a change is detected in the weather condition, the method reverts to the collection 506 of the at least one weather condition, collection 508 of odor level 108, calculation 510 of the odor emission threshold 118, and application 512 of the odor emission threshold 118.

According to one aspect, the method 500 also comprises categorizing the at least one weather condition into a weather condition type. Generally, this categorizing is taken after the selection of the atmospheric dispersion model 504. In one example, the weather condition type is one of the following weather condition types: stable, neutral or unstable.

Although reference has been made throughout the present specification to one emission site, it should be clear to those skilled in the art that in a region where there are multiple odor emission sites, a cumulative odor emission would be received at the remote site(s). Accordingly, for dynamically controlling the odor emission of each individual emission site, a cumulative effect of the odor emissions thereof may need to be considered.

While the present system 100 and method 500 have been shown and described with reference to different aspects thereof, various changes in form and detail may be made herein without departing from the spirit and scope of the invention as defined by the appended claims.

The invention claimed is:

1. A system for dynamically controlling odor emission from an odor emission source, the system comprising:
   an odor measurement tool for measuring an odor level, the odor measuring tool being adapted to replace human senses by means of a sensor array and mathematical algorithms for detecting and quantifying odors;
   a weather condition measurement tool configured for measuring at least one weather parameter and monitoring a change of the at least one weather parameter;
   a processing module configured for dynamically determining an odor emission threshold of said odor emission source, wherein said determining is based on the measured odor level, the measured at least one weather parameter, an atmospheric dispersion model that is a mathematical representation of impacts of weather on odors dispersion in atmosphere and a predetermined remote odor level threshold; and wherein said dynamically determining comprises adjusting the odor emission threshold based on the monitored change of the at least one weather parameter;
   a deodorizer that comprises a burner, a biofilter, a biotrickling filter, a scrubber, a chemical neutralizer, an ion generator, an oxidizer, an incinerator, an absorber, a condenser, a membrane, a catalytic reducer, an ionizer, an ozonator, or an air freshener; and
   a controller configured for dynamically controlling the odor emission of said odor emission source below the odor emission threshold by contacting said deodorizer with compound(s) from said odor emission source that cause(s) said odor emission.

2. The system of claim 1, wherein the odor measurement tool is an electronic nose.

3. The system of claim 2 wherein the at least one weather parameter is chosen from wind velocity, wind direction, wind fluctuation, humidity level, barometric pressure, solar radiation, ambient temperature and an atmospheric stability classification.

4. The system of claim 3, wherein the deodorizer comprises a chemical scrubber.

5. The system of claim 3, wherein the deodorizer comprises a scrubber for use with a disinfectant or ozone.

6. The system of claim 2 wherein the odor emission threshold is further based on at least one odor emission parameter.

7. The system of claim 6 wherein the at least one odor emission parameter is chosen from an emission source type, an emission site height, an emission site diameter, gas speed, gas temperature and a volume flow.

8. The system of claim 7, wherein the deodorizer comprises a chemical scrubber.

9. The system of claim 2 wherein the weather condition measurement tool is remotely located.

10. The system of claim 2, wherein the weather condition measurement tool is co-located with the controller.

11. The system of claim 1, wherein the odor measurement tool and the weather condition measurement tool are co-located.

12. The system of claim 1, wherein the atmospheric dispersion model is chosen from AERMOD, ARIA IMPACT, ARIA RISK, ARIA LOCAL, ARIA INDUSTRY, ARIA REGIONAL, ARCON96, AUSTAL2000, BLP, CAL3QHC/CAL3QHCR, CALINE3, CDM2, COMPLEX1, CTDMPLUS, CTSCREEN, DIMULA, EDMS, ISCST3, ISC-PRIME, KAPPA-G, LONGZ, OCD, OMEGA/ADM, PAL-DS, PPSP, PTPLU, RAM, RTDM3.2, SCREEN3, SDM, SHORTZ, TUPOS, VALLEY, ADMS-3, ADMS-Roads, ADMS-Screen, ADMS-Urban, AEROPOL, AVACTA II, DISPERSION, IFDM, MIMO, OML, OND-86, Simple Line Source, SYMOS97, WYND-VALLEY, CALPUFF, HYSPLIT, MESOPUFF-II, SCIPUFF, CALPUFF View, HOTMAC/RAPTAD, and LADM.

13. The system of claim 1, wherein said processing module is effective for applying at least 7 weather parameters chosen from wind velocity, wind direction, wind fluctuation, solar radiation, humidity level, barometric pressure, ambient temperature and atmospheric stability classification, to the atmospheric dispersion model 14. The system of claim 1, wherein the deodorizer comprises a bioscrubber or a chemical scrubber.

15. A method for dynamically controlling odor emission from an odor emission source, the method comprising:
   collecting remote odor level threshold for at least one remote site;
   monitoring at least one weather parameter;
   measuring an odor level with an odor measuring tool that is adapted to replace human senses by means of a sensor array and mathematical algorithms for detecting and quantifying odors;
   dynamically calculating an odor emission threshold of said odor emission source, said calculating being based on the measured odor level, monitored at least one weather parameter, remote odor level threshold, and an atmospheric dispersion model that is a mathematical representation of impacts of weather on odors dispersion in atmosphere, said dynamically calculating further comprising adjusting the odor emission threshold based on a change of the monitored at least one weather parameter; and
   dynamically controlling the odor emission of said odor emission source below the odor emission threshold by controlling temperature, redox potential, or pH of compound(s) from said odor emission source that cause(s) said odor emission; or by controlling the amount of a chemical reactant, fuel admission, recycling rate of a chemical, or adjustment of air freshener, that is used for treating said compound(s), at said emission source, that cause(s) said odor emission.

16. The method of claim 15 further comprising categorizing the at least one weather parameter into a weather condition type.

17. The method of claim 16 wherein the odor emission threshold is based on the measured odor level, the weather condition type, an atmospheric dispersion model and a predetermined remote odor level threshold.

18. The method of claim 15 wherein the at least one weather parameter is chosen from wind velocity, wind direction, humidity level, barometric pressure, ambient temperature and atmospheric stability classification.

19. The method of claim 18, wherein the dynamically controlling the odor emission of said odor emission source below the odor emission threshold is carried out by controlling the amount of the chemical reactant that is used for treating said compound(s), at said emission source, that cause(s) said odor emission.

20. The method of claim 19, wherein said chemical reactant is chosen from air fresheners, adsorbents, disinfectants, essential oils, perfumes and surfactants.

21. The method of claim 19, wherein said chemical reactant is chosen from ozone, hydrogen peroxide, chlorine and sodium hypochlorite.

22. he system of claim 17 wherein the odor emission threshold is further based on at least one odor emission parameter.

23. The system of claim 22 wherein the at least one odor emission parameter is chosen from an emission source type, an emission site height, an emission site area, gas speed, gas temperature and a volume flow.

24. The method of claim 23, wherein the dynamically controlling the odor emission of said odor emission source below the odor emission threshold is carried out by controlling the amount of the chemical reactant that is used for treating said compound(s), at said emission source, that cause(s) said odor emission.

25. The method of claim 24, wherein said chemical reactant is chosen from air fresheners, adsorbents, disinfectants, essential oils, perfumes and surfactants.

26. The method of claim 24, wherein said chemical reactant is chosen from ozone, hydrogen peroxide, chlorine and sodium hypochlorite.

27. The method of claim 15 wherein the measuring of at least one weather parameter is performed at an odor emission site.

28. The method of claim 15, wherein the atmospheric dispersion model is chosen from AERMOD, ARIA IMPACT, ARIA RISK, ARIA LOCAL, ARIA INDUSTRY, ARIA REGIONAL, ARCON96, AUSTAL2000, BLP, CAL3QHC/ CAL3QHCR, CALINE3, CDM2, COMPLEX1, CTDM-PLUS, CTSCREEN, DIMULA, EDMS, ISCST3, ISC-PRIME, KAPPA-G, LONGZ, OCD, OMEGA/ADM, PAL-DS, PPSP, PTPLU, RAM, RTDM3.2, SCREEN3, SDM, SHORTZ, TUPOS, VALLEY, ADMS-3, ADMS-Roads, ADMS-Screen, ADMS-Urban, AEROPOL, AVACTA II, DISPERSION, IFDM, MIMO, OML, OND-86, Simple Line Source, SYMOS97, WYND-VALLEY, CALPUFF, HYSPLIT, MESOPUFF-II, SCIPUFF, CALPUFF View, HOTMAC/ RAPTAD, and LADM.

29. The method of claim 15, wherein said processing module is effective for applying at least 7 weather parameters chosen from wind velocity, wind direction, wind fluctuation, solar radiation, humidity level, barometric pressure, ambient temperature and atmospheric stability classification, to the atmospheric dispersion model.

30. The method of claim 15, wherein the dynamically controlling the odor emission of said odor emission source below the odor emission threshold is carried out by controlling the amount of the chemical reactant that is used for treating said compound(s), at said emission source, that cause(s) said odor emission.

31. The method of claim 30, wherein said chemical reactant is chosen from air fresheners, adsorbents, disinfectants, essential oils, perfumes and surfactants.

32. The method of claim 30, wherein said chemical reactant is chosen from ozone, calcium carbonate, calcium oxide, magnesium hydroxide, sodium bicarbonate, hydrogen peroxide, chlorine and hypochlorites.

* * * * *